(12) United States Patent
Nutt et al.

(10) Patent No.: US 8,333,952 B2
(45) Date of Patent: Dec. 18, 2012

(54) DOSE SYNTHESIS MODULE FOR BIOMARKER GENERATOR SYSTEM

(75) Inventors: Ronald Nutt, Friendsville, TN (US); Anthony M. Giamis, Knoxville, TN (US); Aaron McFarland, Knoxville, TN (US)

(73) Assignee: ABT Molecular Imaging, Inc., Knoxville, TN (US)

( * ) Notice: Subject to any disclaimer, the term of this patent is extended or adjusted under 35 U.S.C. 154(b) by 345 days.

(21) Appl. No.: 12/565,544

(22) Filed: Sep. 23, 2009

(65) Prior Publication Data

US 2011/0070160 A1    Mar. 24, 2011

(51) Int. Cl.
*A61K 51/00* (2006.01)
*A61M 36/14* (2006.01)

(52) U.S. Cl. .................. 424/1.89; 424/1.81; 422/159
(58) Field of Classification Search ............... 424/1.89
See application file for complete search history.

(56) References Cited

U.S. PATENT DOCUMENTS

| | | | |
|---|---|---|---|
| 2005/0232861 A1 | 10/2005 | Buchanan et al. | |
| 2008/0067413 A1 | 3/2008 | Nutt | |
| 2008/0233018 A1 | 9/2008 | van Dam et al. | |
| 2009/0036668 A1 | 2/2009 | Elizarov et al. | |
| 2010/0145630 A1* | 6/2010 | Ball et al. | 702/31 |
| 2011/0178359 A1* | 7/2011 | Hirschman et al. | 600/4 |

OTHER PUBLICATIONS

Chin et al. J Label. Compd. Radiopharm. 2006, 17-31.*

* cited by examiner

*Primary Examiner* — Michael G Hartley
*Assistant Examiner* — Sean R Donohue
(74) *Attorney, Agent, or Firm* — Pitts & Lake, P.C.

(57) ABSTRACT

A microfluidic radiopharmaceutical production system and process for synthesizing per run approximately, but not less than, one (1) unit dose of a radiopharmaceutical biomarker for use in positron emission tomography (PET). The radiopharmaceutical production system includes a reaction vessel that receives a radioisotope from an accelerator or other radioisotope generator. Organic and aqueous reagents are introduced into the reaction vessel, and the mixture is heated to synthesize a solution of a pre-selected radiopharmaceutical. The radiopharmaceutical solution is purified by passing the solution through a solid phase extraction column and a filter. The synthesis process produces per run a quantity of radiopharmaceutical approximately equal to, but not less than, one (1) unit dose of a radiopharmaceutical, reducing waste and allowing for the production of radiopharmaceutical on an as-needed basis. The synthesis process allows for the production of biomarker radiopharmaceuticals on site and close to the location where the unit dose will be administered to the patient. On-site, as-needed production of radiopharmaceuticals in small doses reduces the time between the synthesis of the radiopharmaceutical and the administration of that radiopharmaceutical, thereby minimizing the loss of active isotopes through decay and allowing the production of lesser amounts of radioisotopes overall.

4 Claims, 5 Drawing Sheets

DOSE SYNTHESIS MODULE FOR BIOMARKER GENERATOR SYSTEM

CROSS-REFERENCE TO RELATED APPLICATIONS

Not Applicable

STATEMENT REGARDING FEDERALLY-SPONSORED RESEARCH OR DEVELOPMENT

Not Applicable

BACKGROUND OF THE INVENTION

1. Field of Invention

This invention concerns a chemical apparatus and process for synthesizing and purifying radiopharmaceuticals for use in positron emission tomography (PET). Specifically, the present invention relates to a system for analyzing a liquid sample of PET biomarker.

2. Description of the Related Art

A biomarker is used to interrogate a biological system and can be created by "tagging" or labeling certain molecules, including biomolecules, with a radioisotope. A biomarker that includes a positron-emitting radioisotope is required for positron-emission tomography (PET), a noninvasive diagnostic imaging procedure that is used to assess perfusion or metabolic, biochemical and functional activity in various organ systems of the human body. Because PET is a very sensitive biochemical imaging technology and the early precursors of disease are primarily biochemical in nature, PET can detect many diseases before anatomical changes take place and often before medical symptoms become apparent. PET is similar to other nuclear medicine technologies in which a radiopharmaceutical is injected into a patient to assess metabolic activity in one or more regions of the body. However, PET provides information not available from traditional imaging technologies, such as magnetic resonance imaging (MRI), computed tomography (CT) and ultrasonography, which image the patient's anatomy rather than physiological images. Physiological activity provides a much earlier detection measure for certain forms of disease, cancer in particular, than do anatomical changes over time.

A positron-emitting radioisotope undergoes radioactive decay, whereby its nucleus emits positrons. In human tissue, a positron inevitably travels less than a few millimeters before interacting with an electron, converting the total mass of the positron and the electron into two photons of energy. The photons are displaced at approximately 180 degrees from each other, and can be detected simultaneously as "coincident" photons on opposite sides of the human body. The modern PET scanner detects one or both photons, and computer reconstruction of acquired data permits a visual depiction of the distribution of the isotope, and therefore the tagged molecule, within the organ being imaged.

Most clinically-important positron-emitting radioisotopes are produced in a cyclotron. Cyclotrons operate by accelerating electrically-charged particles along outward, quasi-spherical orbits to a predetermined extraction energy generally on the order of millions of electron volts. The high-energy electrically-charged particles form a continuous beam that travels along a predetermined path and bombards a target. When the bombarding particles interact in the target, a nuclear reaction occurs at a sub-atomic level, resulting in the production of a radioisotope. The radioisotope is then combined chemically with other materials to synthesize a radiochemical or radiopharmaceutical (hereinafter "radiopharmaceutical") suitable for introduction into a human body. The cyclotrons traditionally used to produce radioisotopes for use in PET have been large machines requiring great commitments of physical space and radiation shielding. These requirements, along with considerations of cost, made it unfeasible for individual hospitals and imaging centers to have facilities on site for the production of radiopharmaceuticals for use in PET.

Thus, in current standard practice, radiopharmaceuticals for use in PET are synthesized at centralized production facilities. The radiopharmaceuticals then must be transported to hospitals and imaging centers up to 200 miles away. Due to the relatively short half-lives of the handful of clinically important positron-emitting radioisotopes, it is expected that a large portion of the radioisotopes in a given shipment will decay and cease to be useful during the transport phase. To ensure that a sufficiently large sample of active radiopharmaceutical is present at the time of the application to a patient in a PET procedure, a much larger amount of radiopharmaceutical must be synthesized before transport. This involves the production of radioisotopes and synthesis of radiopharmaceuticals in quantities much larger than one (1) unit dose, with the expectation that many of the active atoms will decay during transport.

The need to transport the radiopharmaceuticals from the production facility to the hospital or imaging center (hereinafter "site of treatment") also dictates the identity of the isotopes selected for PET procedures. Currently, fluorine isotopes, and especially fluorine-18 (or F-18) enjoy the most widespread use. The F-18 radioisotope is commonly synthesized into [$^{18}$F]fluorodeoxyglucose, or [$^{18}$F]FDG, for use in PET. F-18 is widely used mainly because its half-life, which is approximately 110 minutes, allows for sufficient time to transport a useful amount. The current system of centralized production and distribution largely prohibits the use of other potential radioisotopes. In particular, carbon-11 has been used for PET, but its relatively short half-life of 20.5 minutes makes its use difficult if the radiopharmaceutical must be transported any appreciable distance. Similar considerations largely rule out the use of nitrogen-13 (half-life: 10 minutes) and oxygen-15 (half-life: 2.5 minutes).

As with any medical application involving the use of radioactive materials, quality control is important in the synthesis and use of PET biomarker radiopharmaceuticals, both to safeguard the patient and to ensure the effectiveness of the administered radiopharmaceutical. For example, for the synthesis of [$^{18}$F]FDG from mannose triflate, a number of quality control tests exist. The final [$^{18}$F]FDG product should be a clear, transparent solution, free of particulate impurities; therefore, it is important to test the color and clarity of the final radiopharmaceutical solution. The final radiopharmaceutical solution is normally filtered through a sterile filter before administration, and it is advisable to test the integrity of that filter after the synthesized radiopharmaceutical solution has passed through it. The acidity of the final radiopharmaceutical solution must be within acceptable limits (broadly a pH between 4.5 and 7.5 for [$^{18}$F]FDG, although this range may be different depending upon the application and the radiopharmaceutical tracer involved). The final radiopharmaceutical solution should be tested for the presence and levels of volatile organics, such as ethanol or methyl cyanide, that may remain from synthesis process. Likewise, the solution should be tested for the presence of crown ethers or other reagents used in the synthesis process, as the presence of these reagents in the final dose is problematic. Further, the radiochemical purity of the final solution should be tested to ensure that it is sufficiently high for the solution to be useful. Other tests, such as tests of radionuclide purity, tests for the presence of bacterial endotoxins, and tests of the sterility of the synthesis system, are known in the art.

At present, most or all of these tests are performed on each batch of radiopharmaceutical, which will contain several doses. The quality control tests are performed separately by human technicians, and completing all of the tests typically requires between 45 and 60 minutes.

BRIEF SUMMARY OF THE INVENTION

In the present invention, a PET biomarker production system includes a radioisotope generator, a radiopharmaceutical production module, and a quality control module. PET biomarker production system is designed to produce approximately one (1) unit dose of a radiopharmaceutical biomarker very efficiently. The overall assembly includes a small, low-power cyclotron, particle accelerator or other radioisotope generator (hereinafter "accelerator") for producing approximately one (1) unit dose of a radioisotope. The system also includes a microfluidic chemical production module. The chemical production module or CPM receives the unit dose of the radioisotope and reagents for synthesizing the unit dose of a radiopharmaceutical.

The accelerator produces per run a maximum quantity of radioisotope that is approximately equal to the quantity of radioisotope required by the microfluidic chemical production module to synthesize a unit dose of biomarker. Chemical synthesis using microreactors or microfluidic chips (or both) is significantly more efficient than chemical synthesis using conventional (macroscale) technology. Percent yields are higher and reaction times are shorter, thereby significantly reducing the quantity of radioisotope required in synthesizing a unit dose of radiopharmaceutical. Accordingly, because the accelerator is for producing per run only such relatively small quantities of radioisotope, the maximum power of the beam generated by the accelerator is approximately two to three orders of magnitude less than that of a conventional particle accelerator. As a direct result of this dramatic reduction in maximum beam power, the accelerator is significantly smaller and lighter than a conventional particle accelerator, has less stringent infrastructure requirements, and requires far less electricity. Additionally, many of the components of the small, low-power accelerator are less expensive than the comparable components of conventional accelerators. Therefore, it is feasible to use the low-power accelerator and accompanying CPM within the grounds of the site of treatment. Because radiopharmaceuticals need not be synthesized at a central location and then transported to distant sites of treatment, less radiopharmaceutical need be produced, and different isotopes, such as carbon-11, may be used if desired.

If the accelerator and CPM are in the basement of the hospital or just across the street from the imaging center, then radiopharmaceuticals for PET can be administered to patients almost immediately after synthesis. However, eliminating or significantly reducing the transportation phase does not eliminate the need to perform quality control tests on the CPM and the resultant radiopharmaceutical solution itself. Still, it is essential to reduce the time required to perform these quality control tests in order to take advantage of the shortened time between synthesis and administration. The traditional 45 to 60 minutes required for quality control tests on radiopharmaceuticals produced in macro scale is clearly inadequate. Further, since the accelerator and the CPM are producing a radiopharmaceutical solution that is approximately just one (1) unit dose, it is important that the quality control tests not use too much of the radiopharmaceutical solution; after some solution has been sequestered for testing, enough radiopharmaceutical solution must remain to make up an effective unit dose.

The sample card and quality control module allow operators to conduct quality control tests in reduced time using micro-scale test samples from the radiopharmaceutical solution. The sample card works in conjunction with the CPM to collect samples of radiopharmaceutical solution on the scale of up to 100 microliters per sample. The sample card then interacts with the quality control module (or QCM) to feed the samples into a number of test vessels, where the samples undergo a number of automated diagnostic tests. Because the quality control tests are automated and run in parallel on small samples, the quality control testing process may be completed in under 20 minutes. Further, under the traditional system of macroscale radiopharmaceutical synthesis and quality control testing, a radiopharmaceutical solution would be produced as a batch, and quality control tests would be performed on the entire batch, with each batch producing several doses of radiopharmaceutical. Here, because the PET biomarker production system produces approximately one unit dose per run, at least some quality control tests may be performed on every dose, rather than on the batch as a whole.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A chemical production module and dose synthesis card for a PET biomarker radiopharmaceutical production system are described more fully hereinafter. This invention may, however, be embodied in many different forms and should not be construed as limited to the embodiments set forth herein. Rather, these embodiments are provided to ensure that this disclosure is thorough and complete, and to ensure that it fully conveys the scope of the invention to those skilled in the art.

Figure 1:
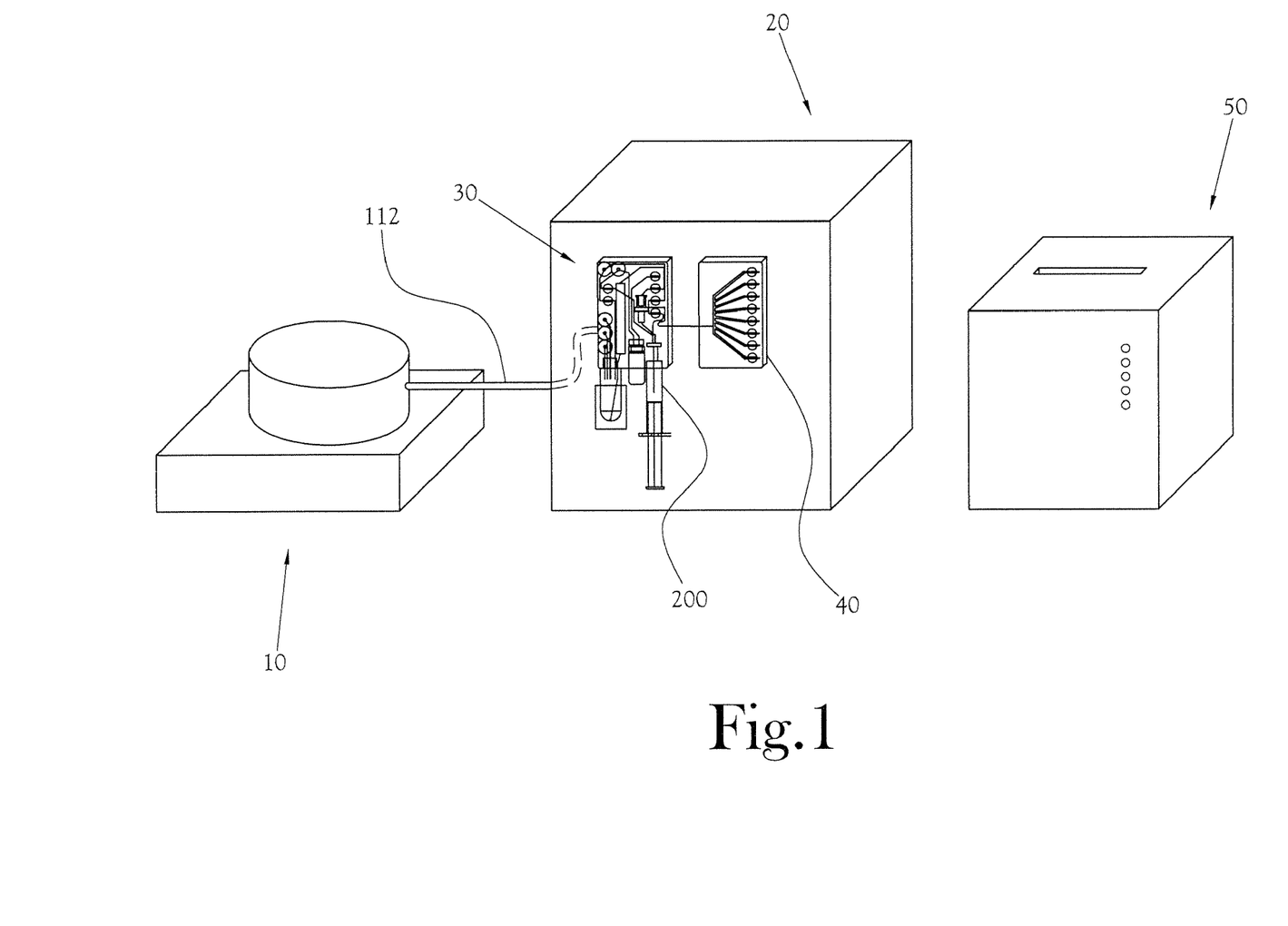
FIG. 1 is an schematic illustration of one embodiment of the overall PET biomarker production system, including the accelerator, the chemical production module (CPM), the dose synthesis card, the sample card, and the quality control module (QCM)
Figure 2:
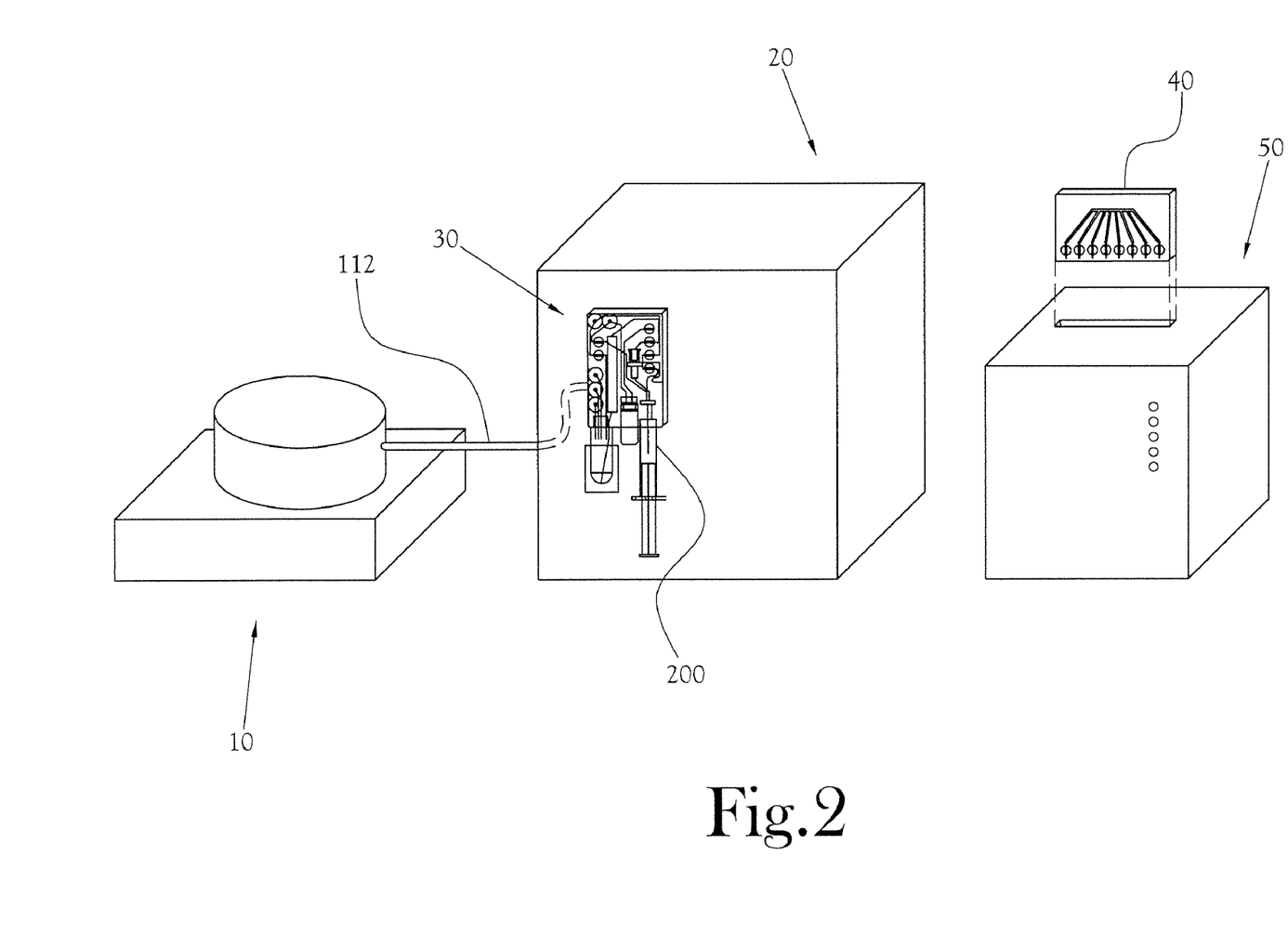
FIG. 2 is another view of the embodiment shown in FIG. 1, showing the sample card interacting with the quality control module (QCM)

The chemical production module, the dose synthesis card and the sample card operate in conjunction with a complete PET biomarker production system. As shown in FIG. 1, one embodiment of this PET biomarker production system comprises an accelerator 10, which produces the radioisotopes; a chemical production module (or CPM) 20; a dose synthesis card 30; a sample card 40; and a quality control module (or QCM) 50. Once the accelerator 10 has produced a radioisotope, the radioisotope travels via a radioisotope delivery tube 112 to the dose synthesis card 30 attached to the CPM 20. The CPM 20 holds reagents and solvents that are required during the radiopharmaceutical synthesis process. In the dose synthesis card 30, the radiopharmaceutical solution is synthesized from the radioisotope and then purified for testing and administration. Following synthesis and purification, a small percentage of the resultant radiopharmaceutical solution is diverted into the sample card 40, while the remainder flows into a dose vessel 200. As shown in FIG. 2, once samples of the radiopharmaceutical solution have flowed into the sample card 40, an operator removes the sample card 40 from the CPM 20 and interfaces it with the QCM 50, where a number of diagnostic instruments perform automated quality control tests on the samples.

Figure 3:
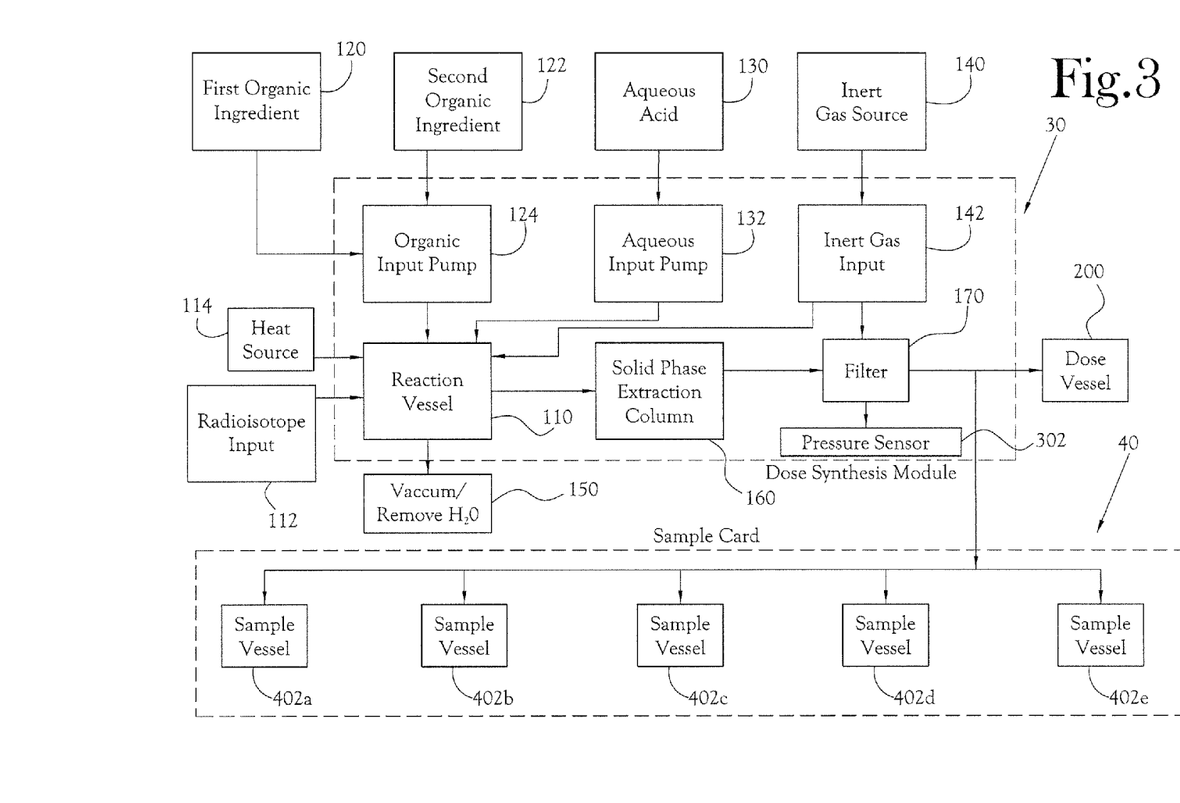
FIG. 3 is a flow diagram of one embodiment of the chemical production module (CPM), the dose synthesis card, and the sample card.
Figure 4:
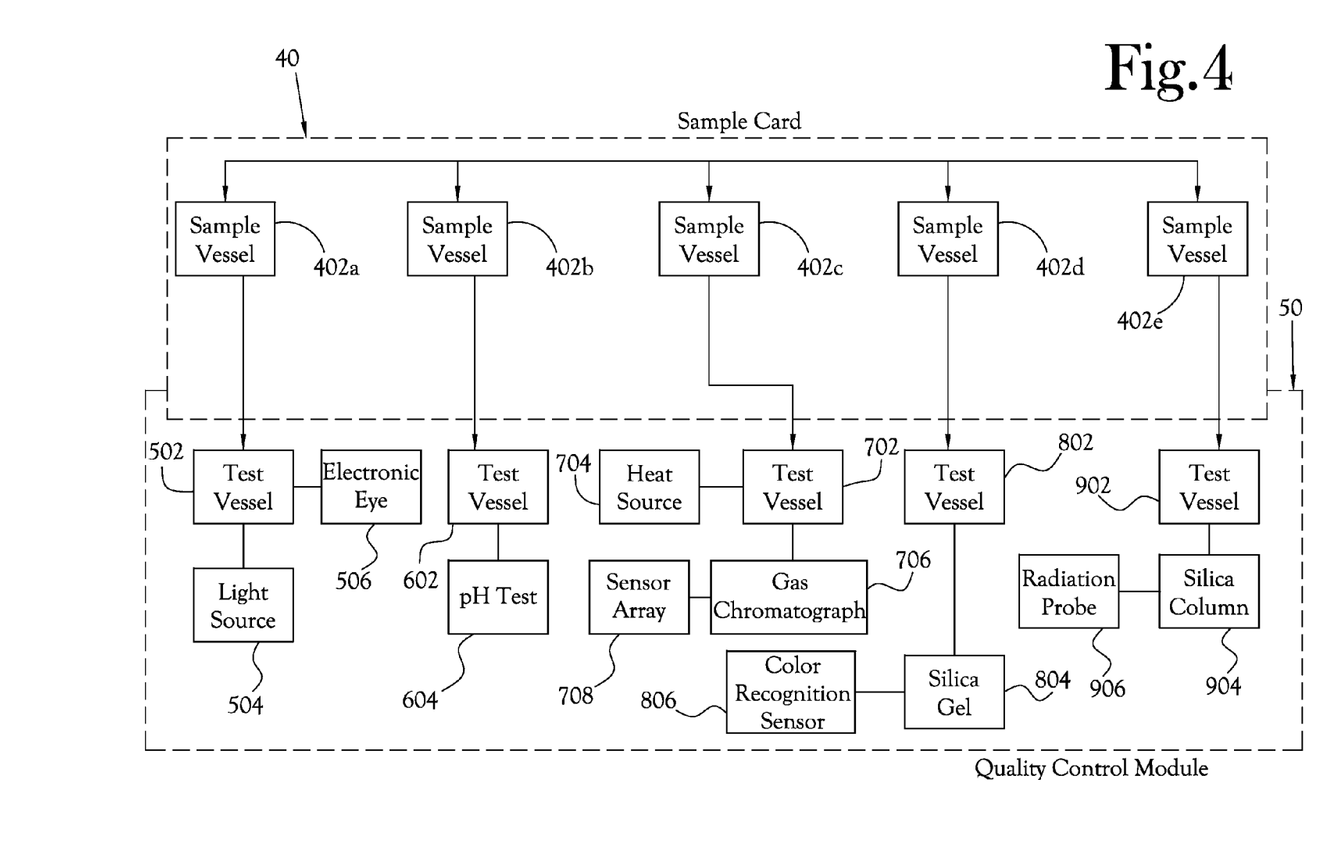
FIG. 4 is a flow diagram of one embodiment of the sample card interacting with one embodiment of the quality control module (QCM)

FIGS. 3 and 4 present a more detailed overview of the complete synthesis and quality control testing processes for one embodiment of the present invention. In this embodiment, the radioisotope involved is flourine-18 (F-18), produced from the bombardment in a cyclotron of heavy water containing the oxygen-18 isotope. However, the sample card and quality control module also work with radiopharmaceutical synthesis systems using other radioisotopes, including carbon-11, nitrogen-13, and oxygen-15.

As shown in FIG. 3, the radioisotope enters a reaction chamber or reaction vessel 110 from the radioisotope delivery tube 112. At this stage, the radioisotope F-18 is still mixed with quantities of heavy water from the biomarker generator. Next, a first organic ingredient is introduced to the reaction vessel 110 from a reagent storage compartment 120 by an organic input pump 124. In some embodiments, the first organic ingredient includes a solution of potassium complexed to 1,10-diaza-4,7,13,16,21,24-hexaoxabicyclo[8.8.8] hexacosane (commonly called Kryptofix 222™, hereinafter "kryptofix") or a similar crown ether. In many embodiments, the potassium-kryptofix complex or similar organometallic complex is carried by acetonitrile as solvent. The potassium activates the F-18 fluoride radioisotope, while the kryptofix binds the potassium atoms and inhibits the formation of a potassium-fluoride complex. Next, a gas input 142 fills the reaction vessel 110 with an inert gas such as dry nitrogen, the gas having been stored in a storage area 140 within or near the CPM 20. Next, the mixture in the reaction vessel 110 is heated by the nearby heat source 114 to remove the residual heavy water by evaporating the azeotropic water/acetonitrile mixture. A vacuum 150 helps to remove the vaporized water. Then, the organic input pump 124 adds a second organic ingredient from a second reagent storage compartment 122 to the mixture in the reaction vessel 110. In many embodiments, the second organic ingredient is mannose triflate in dry acetonitrile. The solution is then heated at approximately 110 degrees Celsius for approximately two minutes. By this stage, the F-18 has bonded to the mannose to form the immediate precursor for [$^{18}$F]FDG, commonly 18F-fluorodeoxyglucose tetraacetate (FTAG). Next, aqueous acid—in many embodiments, aqueous hydrochloric acid—is introduced from a storage compartment 130 through an aqueous input pump 132. The hydrochloric acid removes the protective acetyl groups on the $^{18}$F-FTAG, leaving $^{18}$F-fludeoxyglucose (i.e. [$^{18}$F] FDG).

The [$^{18}$F]FDG having been synthesized, it must be purified before testing and administration. The [$^{18}$F]FDG in solution passes from the reaction vessel 110 through a solid phase extraction column 160. In some embodiments of the present invention, the solid phase extraction column 160 comprises a length filled with an ion exchange resin, a length filled with alumina, and a length filled with carbon-18. The [$^{18}$F]FDG next passes through a filter 170, which in many embodiments includes a Millipore filter with pores approximately 0.22 micrometers in diameter.

Once the radiopharmaceutical solution has passed through the filter 170, some of the solution is diverted into the sample card 40, which contains a number of sample vessels 402a-e, which in some embodiments each hold approximately 10 microliters of solution. The number of sample vessels will vary according to the number of quality control tests to be performed for that run, and the system is adapted to operate with different sample cards containing varying numbers of sample vessels. The remainder of the radiopharmaceutical solution (i.e. all of the solution that is not diverted for quality control testing) flows into the dose vessel 200, ready for administration to a patient.

Once the samples are in the sample vessels 402a-e of the sample card 40, an operator inserts the sample card 40 into the QCM 50, as is shown in FIG. 2. As shown in FIG. 4, the radiopharmaceutical samples travel from the sample vessels 402a-e into the test vessels 502, 602, 702, 802, and 902 within the QCM 50. Within the QCM 50, instruments exist to perform a number of automated quality control tests for each run of radiopharmaceutical produced by the radiopharmaceutical synthesis system.

To test for color and clarity, a light source 504 shines white light through the sample in the test vessel 502. An electronic eye 506 then detects the light that has passed through the sample and measures that light's intensity and color against reference samples.

To test the acidity of the radiopharmaceutical solution, pH test device 604, i.e. a pH probe or pH colorstrip, measures the pH of the sample in the sample vessel 602.

To test for the presence of volatile organics, a heat source 704 heats the sample in the test vessel 702 to approximately 150 degrees Celsius so that the aqueous sample components, now is gas form, enter an adjacent gas chromatograph 706. A gas sensor microarray 708 (informally, an "electronic nose") then detects the presence and prevalence (e.g. as ppm) of such chemicals as methyl cyanide and ethanol.

To test for the presence of kryptofix, the sample in the test vessel 802 is placed on a gel 804 comprising silica gel with iodoplatinate. The sample and gel 804 are then warmed, and a color recognition sensor 806 measures the resultant color of the sample, with a yellow color indicating the presence of kryptofix.

To test the radiochemical purity of the sample, the sample in the test vessel 902 is eluted through a silica column 904 using a carrier mixture of acetonitrile and water. In some embodiments, the acetonitrile and water are mixed in a ratio of 9:1. A radiation probe 906 measures the activity of the solution as it is eluted. As [$^{18}$F]FDG has an elution time that can be predicted with accuracy, the probe 906 measures the percentage of the activity that elutes at or very near to the predicted elution time for [$^{18}$F]FDG. A percentage of 95% or higher indicates acceptable radiochemical purity.

Additionally, a filter integrity test is also performed for every dose that is produced. As shown in FIG. 3, after the radiopharmaceutical solution has gone through the filter 170, the integrity of the filter 170 is tested by passing inert gas from the inert gas input 142 through the filter 170 at increasing pressure. A pressure sensor 302 measures the pressure of the inert gas upon the filter 170 and detects whether the filter 170 is still intact. The filter 170 should be capable of maintaining integrity under pressures of at least 50 pounds per square inch (psi).

Figure 5:
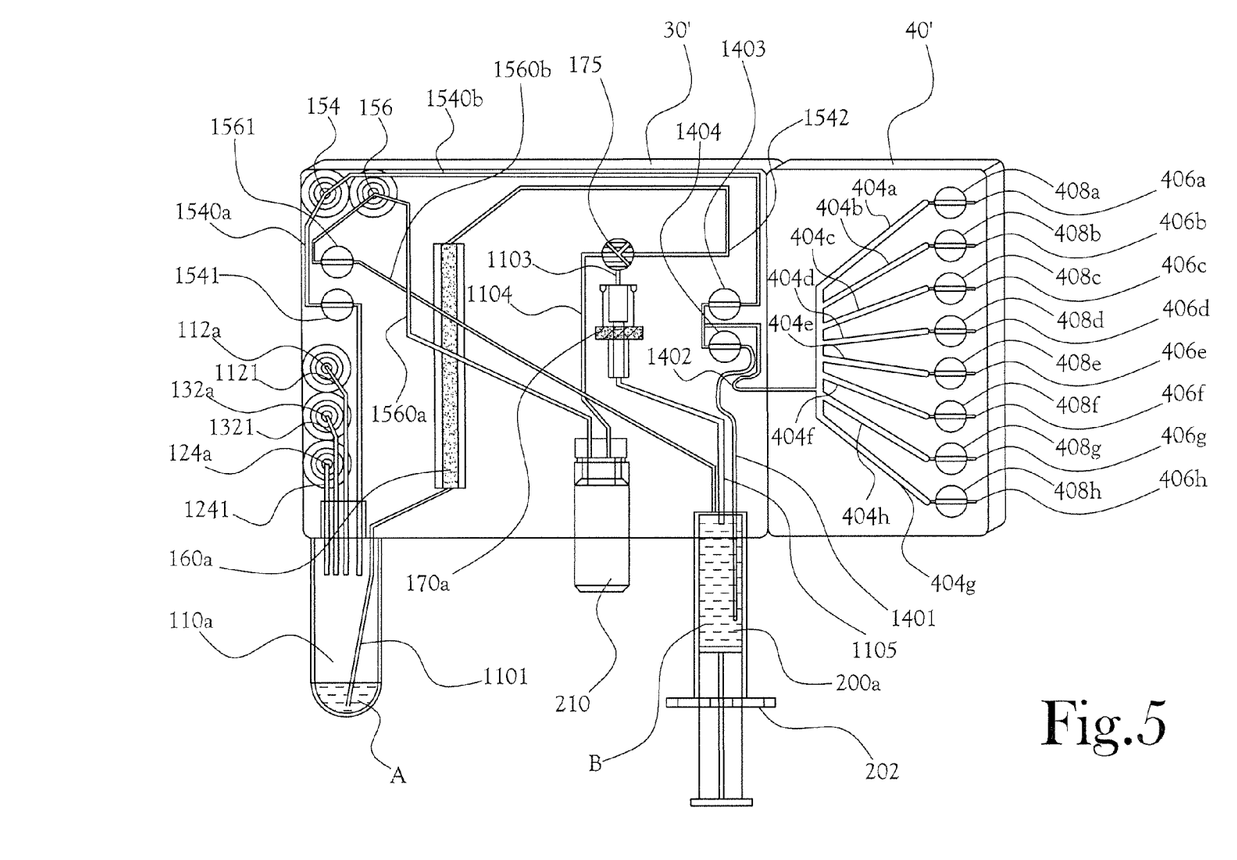
FIG. 5 is a schematic illustration of one embodiment of the dose synthesis card and the sample card.

FIG. 5 displays a schematic view of one embodiment of the dose synthesis card 30' together with the attached sample card 40'. The dose synthesis card 30' includes a reaction vessel 110a where the radiopharmaceutical solution is synthesized. A radioisotope input 112a introduces the radioisotope F-18 into the reaction vessel 110a through a radioisotope input channel 1121. At this stage, the radioisotope is still mixed with quantities of heavy water from the biomarker generator. Next, an organic input 124a introduces a solution of potassium-kryptofix complex in acetonitrile into the reaction vessel 110a through an organic input channel 1241. A combination nitrogen-input and vacuum 154 pumps nitrogen gas into the reaction vessel 110a through a gas channel 1540a and a valve 1541, which valve is at that time in an open position. The mixture A in the reaction vessel 110a is heated in nitrogen atmosphere to azeotropically remove water from the mixture A, the vaporized water being evacuated through the gas channel 1540a and the vacuum 154. Next, the organic input 124a introduces mannose triflate in dry acetonitrile into the reaction vessel 110a through the organic input channel 1241. The solution is heated at approximately 110 degrees Celsius for approximately two minutes. By this stage, the F-18 has bonded to the mannose to form the immediate precursor for [$^{18}$F]FDG, FTAG. Next, aqueous hydrochloric acid is introduced into the reaction vessel 110a through an aqueous input 132a and an aqueous channel 1321. The hydrochloric acid removes the protective acetyl groups on the intermediate $^{18}$F-FTAG, leaving $^{18}$F-fludeoxyglucose (i.e. [$^{18}$F]FDG).

Having been synthesized, the [$^{18}$F]FDG in solution passes from the reaction vessel 110a through a post-reaction channel 1101 into a solid phase extraction column 160a, where some undesirable substances are removed from the solution, thereby clarifying the radiopharmaceutical solution. In some embodiments of the present invention, the solid phase extraction (SPE) column 160a comprises a length with an ion exchange resin, a length filled with alumina, and a length filled with carbon-18. The radiopharmaceutical passes through the SPE column 160a with a mobile phase that in many embodiments includes acetonitrile from the organic input 124a. As some of the mobile phase and impurities emerge from the SPE column 160a, they pass through a second post-reaction channel 1542 and through a three-way valve 175 and waste channel 1104 into a waste receptacle 210. As the clarified radiopharmaceutical solution emerges from the SPE column 160a, the radiopharmaceutical solution next passes through the second post-reaction channel 1542 and through the three-way valve 175 into a filter channel 1103 and then through a filter 170a. The filter 170a removes other impurities (including particulate impurities), thereby further clarifying the radiopharmaceutical solution. In many embodiments the filter 170a includes a Millipore filter with pores approximately 0.22 micrometers in diameter.

Once the radiopharmaceutical solution has passed through the filter 170a, the clarified radiopharmaceutical solution travels via the post-clarification channel 1105 into the sterile dose administration vessel 200a, which in the illustrated embodiment is incorporated into a syringe 202. In some embodiments, the dose administration vessel is filled beforehand with a mixture of phosphate buffer and saline. As the clarified radiopharmaceutical solution fills the sterile dose administration vessel 200a, some of the solution B is diverted through an extraction channel 1401, an open valve 1403, and a transfer channel 1402 into the sample card 40'. The sample card 40' contains a number of sample loops 404a-h, which hold separated aliquots of solution for imminent testing, and a number of valves 408a-h, which at this stage are closed. Once the test-sample aliquots of radiopharmaceutical solution are collected, the sample card 40' is separated from the dose synthesis card 30' and inserted into the QCM, as was shown in FIGS. 2 and 4. The aliquots then travel through the now-open valves 408a-h into the sample egress ports 406a-h, from which the aliquots pass into the test vessels, as was shown in FIG. 4. In the some embodiments, each of the sample loops 404a-h holds approximately 10 microliters of sample solution. The number of sample loops will vary according to the number of quality control tests to be performed for that run, and the system is adapted to operate with different sample cards containing varying numbers of sample loops. After the sample aliquots pass into the sample card 40', any excess solution remaining in the dose administration vessel 200a is extracted by a vent 156 through a first venting channel 1560b and thence conveyed through an open valve 1561 and through a second venting channel 1560a into the waste receptacle 210. The vacuum 154 evacuates residual solution from the transfer channel 1402 through a now-open valve 1403 and a solution evacuation channel 1540b.

In some embodiments of the present invention, the CPM 20 holds sufficient amounts of reagents and solvents that are required during the radiopharmaceutical synthesis process to carry out multiple runs without reloading. Indeed, in some embodiments the CPM 20 is loaded with reagents and solvents approximately once per month, with that month's supply of reagents and solvents sufficient to produce several dozen or even several hundred doses of radiopharmaceutical. As the reagents and solvents are stored in the CPM 20, it is easier than under previous systems to keep the reagents and solvents sterile and uncontaminated. In some embodiments, a sterile environment is supported and contamination inhibited by discarding each dose synthesis card 30 and the sample card 40 after one run; these components of the system are adapted to be disposable.

Thus, each batch of reagents and solvents, loaded periodically into the CPM 20, will supply a batch of multiple doses of radiopharmaceutical, each dose produced in a separate run. Some quality control tests are performed for every dose that is produced, while other quality control tests are performed for every batch of doses. For example, in one embodiment of the present invention, the filter integrity test, the color and clarity test, the acidity test, the volatile organics test, the chemical purity test, and the radiochemical purity test are performed for every dose. On the other hand, some quality control tests need be performed only once or twice per batch, such as the radionuclide purity test (using a radiation probe to measure the half-life of the F-18 in the [$^{18}$F]FDG), the bacterial endotoxin test, and the sterility test. These tests are performed generally on the first and last doses of each batch. Because these per-batch quality control tests are conducted less frequently, they may not be included in the QCM, but rather may be conducted by technicians using separate laboratory equipment.

While the present invention has been illustrated by description of one embodiment, and while the illustrative embodiment has been described in detail, it is not the intention of the applicant to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A microfluidic radiopharmaceutical synthesis system comprising a reaction vessel adapted to receive a radioisotope and at least one reagent, said reaction vessel being in heat-transfer communication with a heat source, whereby when said radioisotope and said at least one reagent are mixed in said reaction vessel and heat is applied to said reaction vessel from said heat source, a radiopharmaceutical solution is synthesized;

a solid-phase extraction column adapted to purify said radiopharmaceutical solution;

a filter adapted to sterilize said radiopharmaceutical solution; and a vessel adapted to receive said radiopharmaceutical solution following its passage through said solid-phase extraction column and said filter, said vessel to hold a quantity of purified radiopharmaceutical solution approximately equal to, but no less than, one (1) unit dose of radiopharmaceutical;

wherein said reaction vessel, said solid-phase extraction column, and said filter are incorporated into a disposable card, said card being discarded after one (1) run, and wherein said system is scaled to produce per run a quantity of purified radiopharmaceutical solution approximately equal to, but no less than, one (1) unit dose of radiopharmaceutical.

2. The system of claim 1 further comprising a sample card adapted to receive multiple aliquots of said purified radiopharmaceutical solution for testing following said purified radiopharmaceutical solution's passage through said solid-phase extraction column and said filter.

3. The system of claim 1 wherein said radioisotope is selected from the group consisting of carbon-11, nitrogen-13, oxygen-15, and fluorine-18.

4. The system of claim 1 wherein said radiopharmaceutical is [$^{18}$F]-2-fluoro-2-deoxy-D-glucose.

* * * * *